United States Patent [19]

Frank

[11] Patent Number: 5,087,785
[45] Date of Patent: Feb. 11, 1992

[54] PROCESSES FOR PREPARING ALKYLATED INDANES AND TETRAHYDRONAPHTHALENES

[75] Inventor: Walter C. Frank, Holland, Pa.

[73] Assignee: Union Camp Corporation, Wayne, N.J.

[21] Appl. No.: 621,688

[22] Filed: Dec. 3, 1990

[51] Int. Cl.$^5$ .................. C07C 2/70; C07C 2/64; C07C 5/22

[52] U.S. Cl. .................. 585/459; 585/446; 585/462; 585/477

[58] Field of Search ............... 585/459, 446, 462, 477

[56] References Cited

U.S. PATENT DOCUMENTS

| | | | |
|---|---|---|---|
| 3,336,407 | 8/1967 | Bushick | 585/477 |
| 4,376,224 | 3/1983 | Gormley | 585/477 |
| 4,466,908 | 8/1984 | Sprecker et al. | 568/330 |

OTHER PUBLICATIONS

Kirk-Othmer, Encycl. of Chem. Tech,., 3rd ed., U.S., pp. 62–67.

*Primary Examiner*—W. J. Shine
*Assistant Examiner*—D. J. McGinty
*Attorney, Agent, or Firm*—William K. Wissing

[57] ABSTRACT

Improved processes for the production of secondary alkyl indanes, particularly mixtures of 1,1,3,5-tetramethyl-3-isopropylindanes and 1,3,3,5-tetramethyl-3-isopropylindane, and alkylated tetrahydronaphthalenes, particularly mixtures of 1,1,3,4,4,6-hexametyl-1,2,3,4-tetrahydronaphthalene and 1,1,2,4,4,6-hexamethyl-1,2,3,4-tetrahydronaphthalene, are described. In the processes of the invention, alkylated tetrahydronaphthalenes or secondary alkyl indanes are isomerized in the presence of a Lewis acid and a solvent which may be a halogenated or unhalogenated solvent and, optionally, a phase transfer agent, to produce, in the case of an alkylated tetrahydronaphthalene starting material, a secondary alkyl indane, and in the case of a secondary alkyl indane starting material, an aklylated tetrahydronaphthalene. The Lewis acid is present in the reaction medium in an amount of less than about 50 mole percent based on the amount of the alkylated tetrahydronaphthalene or secondary alkylindane charged. The subject processes produce the desired compounds at a high rate of reaction, using better, safer, more convenient, or less expensive process methodology than many processes known heretofore.

62 Claims, No Drawings

PROCESSES FOR PREPARING ALKYLATED INDANES AND TETRAHYDRONAPHTHALENES

BACKGROUND OF THE INVENTION

The present invention relates to improved processes for the production of secondary alkyl indanes, particularly mixtures of 1,1,3,5-tetramethyl-3-isopropylindane (IPI) and 1,3,3,5-tetramethyl-1-isopropylindane, and improved processes for the production of alkylated tetrahydronaphthalenes, particularly mixtures of 1,1,3,4,4,6-hexamethyl-1,2,3,4-tetrahydronaphthalene (HMT) and 1,1,2,4,4,6-hexamethyl-1,2,3,4-tetrahydronaphthalene.

Alkylated indanes such as IPI and alkylated tetrahydronaphthalenes such as HMT are of significant importance to the perfumery as well as other industries. By conventional acylation processes, IPI, for example, can be converted to 7-acetyl-1,1,3,5-tetramethyl-3-isopropyl-indane, a well-known musk perfume ingredient. Similarly, HMT can be transformed to 7-acetyl-1,1,3,4,4,6-hexamethyl-1,2,3,4-tetrahydronaphthalene, also a widely recognized musk perfume ingredient. Because of their clean musk fragrance and ability to retain that fragrance over long periods of time, such IPI and HMT derivatives are of great commercial value as synthetic musk perfume substitutes for the expensive, natural musk perfumes of the macrocyclic ketone series. Consequently, various synthetic methods have been proposed for the production of IPI and HMT, as well as other related compounds useful in the perfumery or other industries.

Much research emphasis has been placed on the production of HMT-type compounds. For example, Frank, U.S. Pat. Nos. 4,877,910, 4,877,911, 4,877,912, 4,877,913, 4,877,914, 4,877,915 and 4,877,916, describes processes for producing polyalkyl tetrahydronaphthalene compounds comprising contacting partially substituted benzene compounds such as para-cymene with an olefinic compound such as neohexene or 2,3-dimethyl-1-butene in the presence of one or more of such reagents as alkyl halides or hydrogen halides, Lewis acids, phase transfer agents and hydride abstracting agents.

Wood et al., U.S. Pat. No. 3,856,875, discuss a process for the preparation of HMT wherein an equivalent or excess amount of para-cymene is reacted with a substantially equal molar solution of neohexene and a tertiary alkyl halide in the presence of an effective amount of an anhydrous aluminum halide catalyst suspended in a reaction-compatible solvent.

Wood, U.S. Pat. No. 3,246,044, discloses a process for preparing HMT which includes reacting an alpha,para-dimethylstyrene derivative such as dimethylpara-tolylcarbinyl halide and neohexene in the presence of a catalyst such as aluminum chloride at low temperatures.

Sato et al., U.S. Pat. No. 4,284,818, describe a process for producing HMT comprising reacting paracymene with a 2,3-dimethylbutene using a catalytic amount of anhydrous aluminum halide in the presence of a secondary alkyl halide, tertiary alkyl halide, propargyl halide or allyl halide.

Japanese Patent Publication SHO 57-40420 discusses a method of making HMT characterized by reacting para-cymene and neohexene in the presence of anhydrous aluminum halide as catalyst.

Kahn, U.S. Pat. No. 3,379,785, relates to a process for preparing polyalkyltetrahydronaphthalenes, more specifically, a process for preparing HMT, which involves the reaction of a substituted styrene and a 2,3-dimethylbutene, said reaction being carried out at elevated temperatures and in the presence of a cation exchange resin.

Suzukamo et al., U.S. Pat. No. 4,767,882, disclose a process for preparing a tetrahydronaphthalene derivative in an optically active state which comprises reacting a benzene compound and a pyrocine compound in the presence of a Lewis acid, or, alternatively, reacting a benzene with the pyrocine compound in the presence of an acid catalyst followed by treatment of the resultant production with the Lewis acid.

Some researchers have also focused on the production of IPI-type compounds. For example, Sprecker et al., U.S. Pat. No. 4,466,908, describe a process for preparing indanes such as IPI comprising rearranging hexamethyltetrahydronaphthalene compounds with an aluminum chloride catalyst wherein the reaction is carried out in the presence of tetrachloroethylene solvent saturated with aluminum chloride and in the presence of an excess of aluminum chloride.

Cobb, U.S. Pat. No. 4,551,573, discloses a process for the alkylation of aromatic compounds with olefinic compounds in the presence of a catalyst consisting essentially of aluminum halide and elemental iodine.

Khalaf et al., J. Oro. Chem., Vol. 37, No. 26, pp. 4227–4235 (1972) describes Friedel-Crafts cyclialkylations of certain mono-phenol-substituted and diphenyl-substituted alcohols and alkyl chlorides to produce indane and tetralin compounds. The article also describes the isomerization of tetralins to other tetralin isomers in the presence of aluminum chloride.

Many of these prior art processes suffer from various drawbacks, such as, for example, sluggish reaction rates and high catalyst requirements. New and/or better processes for the production of these compounds are needed. The present invention is directed to these important ends.

SUMMARY OF THE INVENTION

The present invention provides processes for the production of secondary alkyl indanes and alkylated tetrahydronaphthalenes wherein an alkylated tetrahydronaphthalene is isomerized to a secondary alkyl indane or, alternatively, a secondary alkyl indane is isomerized to an alkylated tetrahydronaphthalene, said isomerizations being carried out in the presence of (i) a Lewis acid, and (ii) a solvent which can be a halogenated or unhalogenated solvent and, optionally, (iii) a phase transfer agent, said Lewis acid being present in an amount of less than about 50 mole percent based on the amount of the alkylated tetrahydronaphthalene. The subject processes surprisingly produce the desired compounds at a high rate of reaction, using better, safer, more convenient, or less expensive process methodology than many processes known heretofore.

Specifically, the present invention pertains to a process for producing secondary alkyl indanes, such as those represented by the formula [I]

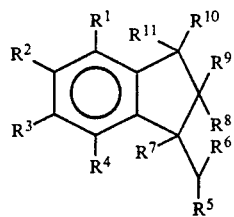

comprising contacting an alkylated tetrahydronaphthalene, such as those represented by the formula [II]

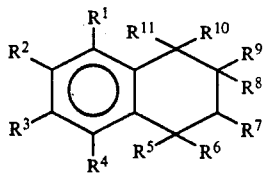

with less than about 50 mole percent of a Lewis acid based on the amount of said alkylated tetrahydronaphthalene, in the presence of a solvent. The solvent can be a halogenated or unhalogenated solvent. If desired, a phase transfer agent may also be employed in the process. In the above formulas [I] and [II], $R^1$, $R^2$, $R^3$, $R^4$, $R^5$, $R^6$, $R^7$, $R^8$, $R^9$, $R^{10}$ and $R^{11}$ are, independently, substituents that do not substantially interfere with a Friedel-Crafts-type alkylation reaction, provided that $R^5$, $R^6$ and $R^7$ are each other than H, and provided that if one of $R^8$ or $R^9$ is H, the other is also H. Using the foregoing process, one is able to produce a variety of secondary alkyl indanes for use as chemical intermediates and/or chemical products, particularly compounds such as 1,1,3,5-tetramethyl-3-isopropylindane and 1,3,3,5-tetramethyl-1-isopropylindane, compounds of significant importance to the fragrance industry.

In addition, the present invention pertains to a process for producing alkylated tetrahydronaphthalenes, such as those represented by the formula [II]

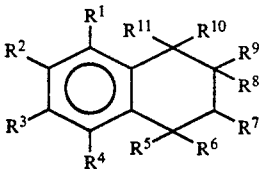

comprising contacting a secondary alkyl indane, such as those represented by the formula [I]

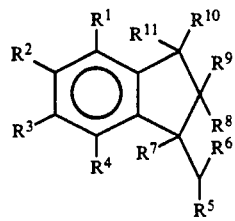

with less than about 50 mole percent of a Lewis acid based on the amount of the secondary alkyl indane, in the presence of a solvent. The solvent can be a halogenated or unhalogenated solvent. If desired, the process may be carried out in the additional presence of a phase transfer agent. In the above formulas [I] and [II], $R^1$, $R^2$, $R^3$, $R^4$, $R^4$, $R^5$, $R^6$, $R^7$, $R^8$, $R^9$, $R^{10}$ and $R^{11}$ are, independently, substituents that do not substantially interfere with a Friedel-Crafts-type alkylation reaction, provided that $R^5$, $R^6$ and $R^7$ are each other than H, and provided that if one of $R^8$ or $R^9$ is H, the other is also H. Using the foregoing process, one is able to produce a variety of alkylated tetrahydronaphthalenes for use as chemical intermediates and/or chemical products, particularly compounds such as 1,1,3,4,4,6-hexamethyl-1,2,3,4-tetrahydronaphthalene and 1,1,2,4,4,6-hexamethyl-1,2,3,4-tetrahydronaphthalene, compounds of significant importance to the fragrance industry.

DETAILED DESCRIPTION OF THE INVENTION

As noted above, the present invention pertains to a novel and particularly useful process for the production of secondary alkyl indanes, including, but not limited to, those of the formula [I]:

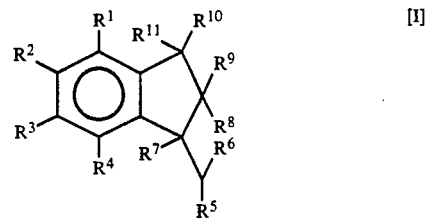

As also noted above, the present invention further pertains to a novel and particularly useful process for the production of alkylated tetrahydronaphthalenes, including, but not limited to, those of formula [II]:

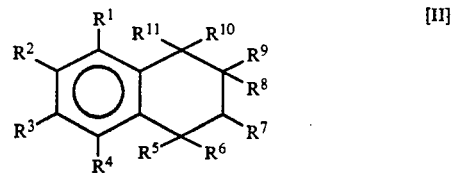

In the above formulas [I] and [II], $R^1$, $R^2$, $R^3$, $R^4$, $R^4$, $R^5$, $R^6$, $R^7$, $R^8$, $R^9$, $R^{10}$ and $R^{11}$ are, independently, as substituents that do not substantially interfere with a Friedel-Crafts-type alkylation reaction, provided that $R^5$, $R^6$ and $R^7$ are each other than H, and provided that if one of $R^8$ or $R^9$ is H, the other is also H. Suitable $R^1$, $R^2$, $R^3$, $R^4$, $R^4$, $R^5$, $R^6$, $R^7$, $R^8$, $R^9$, $R^{10}$ and $R^{11}$ substituents will be readily apparent to those skilled in the art of Friedel-Crafts-type alkylation reactions. Such alkylation reactions and non-interfering substituents are discussed, for example, in George A. Olah, *Friedel-Crafts And Related Reactions*. Vols. 1 and 2 (Interscience Publishers, John Wiley and Sons, 1964) (hereinafter referred to as "*Friedel-Crafts Reactions*"), as well as other journal and textbook references. The disclosures of *Friedel-Crafts Reactions* are incorporated herein in their entirety by reference. Examples of suitable substituents include those wherein $R^1$, $R^2$, $R^3$, $R^4$, $R^4$, $R^5$, $R^6$, $R^7$, $R^8$, $R^9$, $R^{10}$ and $R^{11}$ are, independently, H, or a $C_1$-$C_{30}$ straight chain, branched or cyclical alkyl, and $R^5$, $R^6$, and $R^7$ are, independently, a $C_1$-$C_{30}$ straight chain, branched or cyclical alkyl, provided that if one of $R^8$ or $R^9$ is H, the other is also H. The alkyl is preferably a $C_1$-$C_{20}$, more preferably a $C_1$-$C_{10}$, even more preferably a $C_1$–$C_5$, and most preferably a $C_1$–$C_3$, alkyl. Preferably the alkyl is a straight chain or branched alkyl. In a generally preferred embodiment, $R^2$ and/or $R^3$ are H. In a most preferred embodiment, the secondary alkyl indane is 1,1,3,5-tetramethyl-3-isopropylindane, that is, a compound of formula [I] wherein $R^1$, $R^2$, $R^4$, $R^8$ and $R^9$ are each H, and $R^3$, $R^5$, $R^6$, $R^7$, $R^{10}$ and $R^{11}$ are each methyl, and/or 1,3,3,5-tetramethyl-1-isopropylindane, that is, a compound of formula [I] wherein $R^1$, $R^3$, $R^4$, $R^8$ and $R^9$ are each H, and $R^2$, $R^5$, $R^6$, $R^7$, $R^{10}$ and $R^{11}$ are each methyl, and the alkylated tetrahydronaphthalene is 1,1,3,4,4,6-hexamethyl-1,2,3,4-tetrahydronaphthalene, that is, a compound of formula [II] wherein $R^1$, $R^2$, $R^4$, $R^8$ and $R^9$ are each H, and $R^3$, $R^5$, $R^6$, $R^7$, $R^{10}$ and $R^{11}$ are each methyl, and/or 1,1,2,4,4,6-hexamethyl-1,2,3,4-tetrahydronaphthalene, that is, a compound of formula [II] wherein $R^1$, $R^3$, $R^4$, $R^8$ and $R^9$ are each H, and $R^2$, $R^5$, $R^6$, $R^7$, $R^{10}$ and $R^{11}$ are each methyl.

The compounds of formula [I] are produced by contacting an alkylated tetrahydronaphthalene of the formula [II]

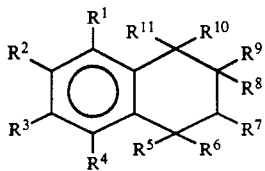

with a Lewis acid in the presence of a solvent which can be a halogenated or unhalogenated solvent. If desired, a phase transfer agent may also be employed in the process.

The compounds of formula [II] are produced by contacting a secondary alkyl indane of the formula [I]

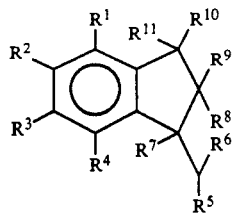

with a Lewis acid in the presence of a solvent Which can be a halogenated or unhalogenated solvent. Optionally, the process is carried out in the additional presence of a phase transfer agent.

Any of the Lewis acids, that is, any non-protonic compounds capable of accepting an electron pair, are suitable for use in the present processes. Exemplary Lewis acids include metal halides such as aluminum halides (including aluminum chloride, aluminum bromide, aluminum iodide, monofluorodichloroaluminum, monobromodichloroaluminum and monoiododichloroaluminum. Alkyl metals and alkyl metal halides suitable for use as Lewis acids in the present process are disclosed, for example, in Kennedy, Joseph P., *Carbocationic Polymerization*, p. 221 (Wiley-Interscience Publishers, 1982), the disclosures of which are incorporated herein by reference. In the processes of the present invention, aluminum halides are preferred. Of the aluminum halides, aluminum chloride and aluminum bromide, particularly aluminum chloride ($AlCl_3$), are most preferred.

In accordance with the invention, the Lewis acid is present in an amount less than about 50 mole percent based on the amount of the alkylated tetrahydronaphthalene charged. Preferably the Lewis acid is present in an amount less than about 40 mole percent, more preferably less than about 30 mole percent, even more preferably less than about 20 mole percent, and most preferably is present in an amount equal to about 10 mole percent, all based on the amount of the alkylated tetrahydronaphthalene or secondary alkyl indane starting material.

Halogenated solvents suitable for use in the present process are varied, and include halogenated aliphatic, halogenated alicyclic and halogenated aromatic hydrocarbon solvents. Particularly preferred are the halogenated aliphatic hydrocarbons. Suitable halogenated solvents include, for example, 1,2-dichloroethane, 1,1-dichloroethane, trichloromethane, dichloromethane, 1,1,2,2-tetrachloroethylene, 1,2-dichloroethylene, 1,2,3-trichloropropane, 1,1,2-trichloroethane, monochlorobenzene, fluorobenzene, and ortho-dichlorobenzene. Particularly preferred halogenated solvents include dichloromethane, trichloromethane and 1,2-dichloroethane.

As an alternative to or in combination with halogenated solvents, one may employ unhalogenated solvents. A variety of unhalogenated solvents may be utilized in the present invention, including, unhalogenated aliphatic, unhalogenated alicyclic and unhalogenated aromatic hydrocarbon solvents. Such unhalogenated solvents are generally preferred over the halogenated solvents for reasons of safety. Particularly preferred are the unhalogenated aliphatic and unhalogenated alicyclic hydrocarbons. Suitable unhalogenated solvents include, for example, the aliphatic hydrocarbon solvents n-hexane, n-heptane and n-octane, the alicyclic hydrocarbon solvent cyclohexane, and aromatic hydrocarbon solvents, such as mesitylene. A particularly preferred unhalogenated solvent is the unhalogenated alicyclic hydrocarbon solvent cyclohexane.

Phase transfer agents suitable for use in the present invention include onium salts such as ammonium, phosphonium and sulfonium salts. Other phase transfer agents suitable for use in the present process will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridecylbenzylammonium chloride, and homologues thereof having chlorine, fluorine, bromine or iodine atoms substituted for the enumerated halide atom.

Exemplary phosphonium phase transfer agents include quaternary phosphonium halides such as tributyldecylphosphonium iodide, triphenyldecylphosphonium iodide, tributylhexadecylphosphonium iodide, and homologues thereof having chlorine, fluorine or bromine atoms substituted for the iodine atom.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom.

These and other suitable phase transfer agents are described, for example, in Napier et al., U.S. Pat. No. 3,992,432 entitled "Phase Transfer Catalysis of Heterogenous Reactions by Quaternary Salts", and in Kondo et al., *Synthesis.* pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride, and a mixture of methyltrioctylammonium chloride and methyltridecylammonium chloride. The latter mixture is marketed under the trademark Adogen-464, by Sherex Co., located in Dublin, Ohio.

In general, the molar proportions of the reagents employed in the present process can be varied over a relatively wide range, provided that the Lewis acid is present in an amount of less than about 50 mole percent based on the amount of the alkylated tetrahydronaphthalene or secondary alkyl indane starting material. As previously noted, it is preferable that the Lewis acid be present in an amount of less than about 40 mole percent, more preferably less than about 30 mole percent, even more preferably less than about 20 mole percent, and most preferably in an amount equal to about 10 mole percent, all based on the amount of alkylated tetrahydronaphthalene or secondary alkyl indane starting material. Of course within these parameters, the amount of Lewis acid will depend in part on the particular solvent employed, the presence or absence of a phase transfer agent, and the specific tetrahydronaphthalene starting material and other reaction conditions such as time, temperature, pressure, etc. The particular amount to be employed will be well within the ambit of those skilled in the art, once armed with the present disclosures.

It has been surprisingly found, however, that it is helpful to minimize the amount of solid Lewis acid catalyst present in the reaction medium. As an important feature in accomplishing this goal, the amount of the Lewis acid should be kept reasonably low, that is, the amount should be kept below about 50 mole percent based on the amount of the tetrahydronaphthalene or indane starting material, as previously described. Also helpful in minimizing the amount of solid Lewis acid catalyst present in the reaction medium is the use of a phase transfer agent and/or a solvent. Such phase transfer agents and solvents will assist in liquifying and/or solubilizing the Lewis acid catalyst. Indeed, it has been surprisingly found in the present invention that the existence of an excess of solid Lewis acid catalyst such as that urged in Sprecker et al. U.S. Pat. No. 4,466,908 for the preparation of isopropyl tetramethyl indane compounds, fails to serve any beneficial chemical purpose in such reactions. In fact, the presence of excess solid catalyst is detrimental in that it leads to greater reactor corrosion problems, less uniform reaction rates, various chemical engineering difficulties, and poses environmental concerns. Contrary to the suggestions in Sprecker et al., the process of the present invention provides a reaction that proceeds rapidly and efficiently to yield the desired end products.

Although varying amounts of the other process constituents can be employed, for best results, however, it is important to maintain a ratio of less than one mole of phase transfer agent per mole of Lewis acid. Preferably, the molar ratio is about 0.8 to 1.0, more preferably about 0.5 to 1.0, phase transfer agent to Lewis acid. It should be noted that some phase transfer agents sold commercially are sold in an impure form. Such impurities usually comprise water or an alcohol species. Water and alcohol, as well as other impurities, will react adversely with the Lewis acid, thereby lowering the amount of Lewis acid available for the process of the present invention. Accordingly, where the phase transfer agent added contains such impurities, the amount of Lewis acid should be increased to account for these impurities. In such a situation, the ratio of transfer agent to Lewis acid might be about 0.3 to 1.0. Such impure agent-containing mixtures are referred to herein as mixtures in an "impure form".

The isomerization reaction of the invention can be carried out in any suitable vessel which provides sufficient contacting between the Lewis acid, the phase transfer agent and the other reactants. For simplicity, a stirred batch reactor can be employed. Although stirring is recommended to provide efficient contact between reactants, it has been found that in the halogenated solvent, or in the unhalogenated solvent plus phase transfer agent, the Lewis acid is able to solubilize and/or liquify rather quickly, thereby obviating the need for stringent stirring requirements. The reaction vessel used should be resistant to the possible corrosive nature of the Lewis acid. Glass-lined vessels are suitable for this purpose, as well as other vessel materials well-known in the art.

The reagents of the present process may be added to the vessel in any order, although generally the solvent, the alkylated tetrahydronaphthalene or secondary alkyl indane, and any phase transfer agent are added first, followed by Lewis acid addition.

Ideally, the reaction is carried out at temperatures ranging from about $-30°$ C. to about $50°$ C., preferably temperatures ranging from about $-10°$ C. to about $30°$ C., and most preferably at temperatures ranging from about $0°$ C. to about $20°$ C.

The pressure at which the reaction is carried out is not critical. If the reaction is carried out in a sealed vessel, autogenous pressure is acceptable, although higher or lower pressures, if desired, may be employed. The reaction may also be carried out at atmospheric pressure in an open reaction vessel, in which case, the vessel is preferably equipped with a moisture trap to prevent significant exposure of Lewis acid to moisture. The reaction may take place in an oxygen atmosphere or an inert atmosphere, as in the presence of a gas such as nitrogen, argon and the like, the type of atmosphere also not being critical.

Reaction time is generally rather short and is often dictated by the type of equipment employed. Sufficient time should be provided, however, for thorough contacting of the alkylated tetrahydronaphthalenes or secondary alkyl indane starting materials, the Lewis acid, the solvent, and any phase transfer employed. Generally, the isomerization reaction of the present invention proceeds to equilibrium in about 1 to about 8 hours.

As those skilled in the art would recognize, simple alkyl migrations from one aromatic ring carbon to another within an aromatic nucleus can occur when Friedel-Crafts-type conditions are employed. Thus, for example, when HMT is employed as the starting material in the subject process, migration of a methyl group from its original $R^3$ position in formula I to the $R^2$ position in that formula before isomerization to the corresponding indane of formula II can result in a reaction product mixture containing both IPI and 1,3,3,5-tetramethyl-1-isopropylindane. Similarly, migration of a methyl group in the IPI product following isomerization can result in a reaction product mixture containing again not only IPI but also 1,3,3,5-tetramethyl-1-isopropylindane.

Product can be recovered from the reaction mixture by first quenching the reaction mixture in cold water or on crushed ice, preferably on ice, and then processing the mixture in the usual manner for Friedel-Crafts reactions to extract the desired secondary alkyl indane or alkylated tetrahydronaphthalene compounds. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. The resultant product is generally a mixture of the alkylated tetrahydronaphthalene or secondary alkyl starting material and the desired isomerates. A more purified product can be obtained by subjecting the washed reaction mixture to reduced pressure fractional distillation, commercial chromatographic separation or other separation means known to those skilled in the art.

The secondary alkyl indanes or alkylated tetrahydronaphthalenes prepared in accordance with the processes of the invention may then, for example, be acylated to obtain acylated alkylated secondary alkyl indanes or acylated alkylated tetrahydronaphthalenes having very fine, musk-like fragrances, a characteristic which renders them highly valuable for use in the perfumery industry. Such products, acylated or otherwise, may alternatively or additionally have utility in the pharmaceutical and/or agrochemical industries, either as intermediates or as end products, as generally discussed in French Patent Publication No. 2601670, and U.S. Pat. No. 4,551,573. The acylation process may be carried using conventional methods, such as by reacting the secondary alkyl indanes with an acyl halide or acid anhydride in the presence of an acid-acting catalyst. Suitable acylation methods are well known in the art and are described, for example, in U.S. Pat. No. 4,284,818, the disclosures of which are incorporated herein by reference. An example of an acylated alkylated secondary alkyl indane includes 7-acetyl-1,1,3,5-tetramethyl-3-isopropylindane, and an example of an acylated alkylated tetrahydronaphthalene is 7-acetyl-1,1,3,4,4,6-hexamethyl-1,2,3,4-tetrahydronaphthalene.

The present invention is further described in the following Examples. These Examples are not to be construed as limiting the scope of the appended claims.

In each Example, the reaction flasks were equipped with a condenser, mechanical stirrer, addition funnel and thermocouple/temperature controller connected to an automatic laboratory jack. The flasks were cooled, when necessary, with a dry ice/isopropanol bath. The flask contents were continuously stirred throughout the reaction.

Results were analyzed on both polar and non-polar gas chromatography columns. All gas chromatography analyses were carried on capillary columns using a weight percent internal standard method of analysis. Structural identifications were assigned based on GCMS fragmentation patterns compared to standards.

Examples 1 through 3 below are examples of processes of the present invention. Example 4 below is provided for comparative purposes only, and does not illustrate processes of the present invention. Example 4 was carried out substantially in accordance With the procedures set forth in Sprecker et al., U.S. Pat. No. 4,466,908.

EXAMPLE 1

A 100 ml four-necked round bottom flask was charged with 1,1,3,4,4,6-hexamethyl-1,2,3,4-tetrahydronaphthalene (HMT) (20.0 g) and dichloromethane (32.6 g) and cooled to 0° C. with a dry ice/isopropanol bath. To the flask was then added, with stirring, anhydrous $AlCl_3$ (2.507 g; 20.3 mole percent $AlCl_3$ based on the amount of HMT charged). The temperature of the flask was maintained between about 0 C and about 10° C. while the reaction was allowed to proceed for about 2.5 hours. The reaction was then quenched with ice water (25 ml), and the resultant product washed with deionized water. The aqueous layer was extracted twice with ether, the organics were combined, dried over $K_2CO_3$ and rotoevaporated to yield a crude product (18.26 g) containing 37.22 weight percent of a mixture of 1,1,3,5-tetramethyl-3-isopropylindane and 1,3,3,5-tetramethyl-1-isopropylindane.

EXAMPLE 2

A 25 ml three-necked round bottom flask was charged with 1,1,3,4,4,6-hexamethyl-1,2,3,4-tetrahydronaphthalene (HMT) (5.02 g) and dichloromethane (8.16 g) and cooled to 0° C. To the flask was then added $AlCl_3$ (0 625 g; 20.2 mole percent $AlCl_3$ based on the amount of HMT charged). The temperature of the flask was maintained at about 0° C. while the reaction was allowed to proceed for about 5 hours. The reaction was then quenched with ice water (10 ml), the aqueous layer was extracted twice With ether, and the resultant product was washed with deionized water. The organics were combined, dried over $K_2CO_3$ and rotoevaporated to yield a crude product (4.21 g) containing 36.50 weight percent of a mixture of 1,1,3,5-tetramethyl-3-isopropylindane and 1,3,3,5-tetramethyl-1-isopropylindane.

EXAMPLE 3

A 25 ml three-necked round bottom flask was charged with cyclohexane (4.83 g) and 1,1,3,4,4,6-hexamethyl-1,2,3,4-tetrahydronaphthalene (HMT) (5.03 g) and cooled to 10° C. with a dry ice/isopropanol bath. To the flask was then added, with stirring, methyltrioctylammonium chloride (0.47 g). Next, anhydrous $AlCl_3$ (1.54 g; 50 mole percent $AlCl_3$ based on the amount of HMT charged) was added and the reaction was allowed to proceed for about 2 hours during which time the temperature of the flask was maintained at about 10° C. The reaction was then quenched over ice (50 ml), and the layers were separated. The aqueous portion was extracted twice with dichloromethane (75 ml per extraction), the organics were combined and the resultant product washed with deionized water and dried over $K_2CO_3$ to yield a crude product (5.25 g) after rotoevaporation containing 43.52 weight percent of a mixture of 1,1,3,5-tetramethyl-3-isopropylindane and 1,3,3,5-tetramethyl-3-isopropylindane.

EXAMPLE 4 (COMPARATIVE EXAMPLE)

A 25 ml three-necked round bottom flask was charged with tetrachloroethylene (50.50 g) and 1,1,3,4,4,6-hexamethyl-1,2,3,4-tetrahydronaphthalene (HMT) (25.50 g) and cooled to 0° C. To the flask was then added AlCl$_3$ (17.5 g; 111.1 mole percent AlCl$_3$ based on the amount of HMT charged). The temperature of the flask was maintained at about 0° C. while the reaction was allowed to proceed for about 7 hours. The reaction was then quenched with ice water (500 ml), and the layers were separated. The aqueous portion was extracted twice with dichloromethane (75 ml per extraction). The organics were combined, and the resultant product washed with deionized water, dried over K$_2$CO$_3$ and rotoevaporated to yield a crude product (22.46 g) containing 10.0 weight percent of a mixture of 1,1,3,5-tetramethyl-3-isopropylindane and 1,3,3,5-tetramethyl-3-isopropylindane.

Various modifications of the invention, in addition to those shown and described herein, will be apparent to those skilled in the art from the foregoing description. Such modifications are also intended to fall within the scope of the appended claims.

What is claimed is:

1. A process for producing a secondary alkyl indane compound comprising
   contacting an alkylated tetrahydronaphthalene compound,
   with less than about 50 mole percent of a Lewis acid based on the amount of said alkylated tetrahydronaphthalene compound,
   in the presence of a solvent.

2. A process for producing a secondary alkyl indane compound of the formula

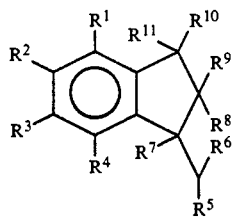

comprising contacting an alkylated tetrahydronaphthalene compound of the formula

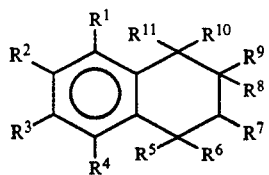

with less than about 50 mole percent of a Lewis acid based on the amount of said alkylated tetrahydronaphthalene compound,
in the presence of a solvent,
wherein in the above formulas $R^1$, $R^2$, $R^3$, $R^4$, $R^5$, $R^6$, $R^7$, $R^8$, $R^9$, $R^{10}$ and $R^{11}$ are independently, substituents that do not substantially interfere with an alkylation reaction, provided that $R^5$, $R^6$ and $R^7$ are each other than H, and provided that if one of $R^8$ or $R^9$ is H, the other is also H.

3. A process of claim 2 wherein $R^1$, $R^2$, $R^4$, $R^8$, $R^9$, $R^{10}$ and $R^{11}$ are, independently, H, or a C$_1$-C$_{30}$ straight chain, branched or cyclical alkyl, and $R^5$, $R^6$ and $R^7$ are, independently, a C$_1$-C$_{30}$ straight chain, branched or cyclical alkyl.

4. A process of claim 3 wherein said alkyl is a straight chain or branched alkyl.

5. A process of claim 3 wherein said alkyl is a C$_1$-C$_3$ alkyl.

6. A process of claim 5 wherein $R^2$ is H.

7. A process of claim 5 wherein $R^3$ is H.

8. A process of claim 3 wherein $R^1$, $R^2$, $R^4$, $R^8$ and $R^9$ are each H, and $R^3$, $R^5$, $R^6$, $R^7$, $R^{10}$ and $R^{11}$ are each methyl.

9. A process of claim 3 wherein $R^1$, $R^3$, $R^4$, $R^8$ and $R^9$ are each H, and $R^2$, $R^5$, $R^6$, $R^7$, $R^{10}$ and $R^{11}$ are each methyl.

10. A process of claim 2 wherein said Lewis acid is selected from the group consisting of metal halides, alkyl metal halides and alkyl metals.

11. A process of claim 10 wherein said Lewis acid is a metal halide which is an aluminum halide.

12. A process of claim 11 wherein said aluminum halide is AlCl$_3$.

13. A process of claim 2 wherein said solvent is a halogenated solvent.

14. A process of claim 13 wherein said halogenated solvent is selected from the group consisting of halogenated aliphatic hydrocarbon solvents, halogenated alicyclic hydrocarbon solvents and halogenated aromatic hydrocarbon solvents.

15. A process of claim 14 wherein said halogenated solvent is a halogenated aliphatic hydrocarbon solvent.

16. A process of claim 15 wherein said halogenated aliphatic hydrocarbon solvent is selected from the group consisting of dichloromethane, trichloromethane and 1,2-dichloroethane.

17. A process of claim 13 further comprising carrying out said process in the presence of a phase transfer agent.

18. A process of claim 17 wherein said phase transfer agent is selected from the group consisting of ammonium, phosphonium and sulfonium salts.

19. A process of claim 18 wherein said phase transfer agent is an ammonium salt which is a quaternary ammonium halide.

20. A process of claim 19 wherein said quaternary ammonium halide is methyltrioctylammonium chloride.

21. A process of claim 19 wherein said quaternary ammonium halide is a mixture of methyltrioctylammonium chloride and methyltridecylammonium chloride.

22. A process of claim 2 wherein said solvent is an unhalogenated solvent.

23. A process of claim 22 wherein said unhalogenated solvent is selected from the group consisting of unhalogenated aliphatic hydrocarbon solvents, unhalogenated alicyclic hydrocarbon solvents and unhalogenated aromatic hydrocarbon solvents.

24. A process of claim 23 wherein said unhalogenated solvent is selected from the group consisting of unhalogenated aliphatic hydrocarbon solvents, and unhalogenated alicyclic hydrocarbon solvents.

25. A process of claim 24 wherein said unhalogenated solvent is an unhalogenated alicyclic hydrocarbon solvent which is cyclohexane.

26. A process of claim 22 further comprising carrying out said process in the presence of a phase transfer agent.

27. A process of claim 26 wherein said phase transfer agent is selected from the group consisting of ammonium, phosphonium and sulfonium salts.

28. A process of claim 27 wherein said phase transfer agent is an ammonium salt which is a quaternary ammonium halide.

29. A process of claim 28 wherein said quaternary ammonium halide is methyltrioctylammonium chloride.

30. A process of claim 28 wherein said quaternary ammonium halide is a mixture of methyltrioctylammonium chloride and methyltridecylammonium chloride.

31. A process for producing 1,1,3,5-tetramethyl-3-isopropylindane comprising
contacting 1,1,3,4,4,6-hexamethyl-1,2,3,4-tetrahydronaphthalene,
with less than about 30 mole percent AlCl₃ based on the amount of said 1,1,3,4,4,6-hexamethyl1,2,3,4-tetrahydronaphthalene,
in the presence of cyclohexane, and
further in the presence of a quaternary ammonium halide.

32. A process for producing an alkylated tetrahydronaphthalene compound comprising
contacting a secondary alkyl indane compound,
with less than about 50 mole percent of a Lewis acid based on the amount of said secondary alkyl indane compound,
in the presence of a solvent.

33. A process for producing an alkylated tetrahydronaphthalene compound of the formula

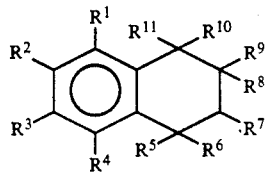

comprising contacting a secondary alkyl indane compound of the formula

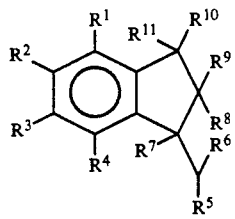

with less than about 50 mole percent of a Lewis acid based on the amount of said secondary alkyl indane compound,
in the presence of a solvent,
wherein in the above formulas $R^1$, $R^2$, $R^3$, $R^4$, $R^5$, $R^6$, $R^7$, $R^8$, $R^9$, $R^{10}$ and $R^{11}$ are, independently, substituents that do not substantially interfere with an alkylation reaction, provided that $R^5$, $R^6$ and $R^7$ are each other than H, and provided that if one of $R^8$ or $R^9$ is H, the other is also H.

34. A process of claim 33 wherein $R^1$, $R^2$, $R^3$, $R^4$, $R^8$, $R^9$, $R^{10}$ and $R^{11}$ are, independently, H, or a $C_1$–$C_{30}$ straight chain, branched or cyclical alkyl, and $R^5$, $R^6$ and $R^7$ are, independently, a $C_1$–$C_{30}$ straight chain, branched or cyclical alkyl.

35. A process of claim 34 wherein said alkyl is a straight chain or branched alkyl.

36. A process of claim 34 wherein said alkyl is a $C_1$–$C_3$ alkyl.

37. A process of claim 36 wherein $R^2$ is H.

38. A process of claim 36 wherein $R^3$ is H.

39. A process of claim 34 wherein $R^1$, $R^2$, $R^4$, $R^8$ and $R^9$ are each H, and $R^3$, $R^5$, $R^6$, $R^7$, $R^{10}$ and $R^{11}$ are each methyl.

40. A process of claim 34 wherein $R^1$, $R^3$, $R^4$, $R^8$ and $R^9$ are each H, $R^2$, $R^5$, $R^6$, $R^7$, $R^{10}$ and $R^{11}$ are each methyl.

41. A process of claim 33 wherein said Lewis acid is selected from the group consisting of metal halides, alkyl metal halides and alkyl metals.

42. A process of claim 41 wherein said Lewis acid is a metal halide which is an aluminum halide.

43. A process of claim 42 wherein said aluminum halide is AlCl₃.

44. A process of claim 33 wherein said solvent is a halogenated solvent.

45. A process of claim 44 wherein said halogenated solvent is selected from the group consisting of halogenated aliphatic hydrocarbon solvents, halogenated alicyclic hydrocarbon solvents and halogenated aromatic hydrocarbon solvents.

46. A process of claim 45 wherein said halogenated solvent is a halogenated aliphatic hydrocarbon solvent.

47. A process of claim 46 wherein said halogenated aliphatic hydrocarbon solvent is selected from the group consisting of dichloromethane, trichloromethane and 1,2-dichloroethane.

48. A process of claim 44 further comprising carrying out said process in the presence of a phase transfer agent.

49. A process of claim 48 wherein said phase transfer agent is selected from the group consisting of ammonium, phosphonium and sulfonium salts.

50. A process of claim 49 wherein said phase transfer agent is an ammonium salt which is a quaternary ammonium halide.

51. A process of claim 50 wherein said quaternary ammonium halide is methyltrioctylammonium chloride.

52. A process of claim 50 wherein said quaternary ammonium halide is a mixture of methyltrioctylammonium chloride and methyltridecylammonium chloride.

53. A process of claim 33 wherein said solvent is an unhalogenated solvent.

54. A process of claim 53 wherein said unhalogenated solvent is selected from the group consisting of unhalogenated aliphatic hydrocarbon solvents, unhalogenated alicyclic hydrocarbon solvents and unhalogenated aromatic hydrocarbon solvents.

55. A process of claim 54 wherein said unhalogenated solvent is selected from the group consisting of unhalogenated aliphatic hydrocarbon solvents and unhalogenated alicyclic hydrocarbon solvents.

56. A process of claim 55 wherein said unhalogenated solvent is an unhalogenated alicyclic hydrocarbon solvent which is cyclohexane.

57. A process of claim 53 further comprising carrying out said process in the presence of a phase transfer agent.

58. A process of claim 57 wherein said phase transfer agent is selected from the group consisting of ammonium, phosphonium, and sulfonium salts.

59. A process of claim 58 wherein said phase transfer agent is an ammonium salt which is a quaternary ammonium halide.

60. A process of claim 59 wherein said quaternary ammonium halide is methyltrioctylammonium chloride.

61. A process of claim 60 wherein said quaternary ammonium halide is a mixture of methyltrioctylammonium chloride and methyltridecylammonium chloride.

62. A process for producing 1,1,3,4,4,6-hexamethyl-1,2,3,4-tetrahydronaphthalene comprising contacting 1,3,5-tetramethyl-3-isopropylindane,
  with less than about 30 mole percent $AlCl_3$ based on the amount of said 1,1,3,5-tetramethyl-3-isopropylindane,
in the presence of cyclohexane, and
further in the presence of a quaternary ammonium halide.

* * * * *